United States Patent [19]
Wollweber et al.

[11] 3,960,890

[45] *June 1, 1976

[54] FLUOROALKYLPHENYLCYCLOAMIDINES AND THEIR PRODUCTION

[75] Inventors: Hartmund Wollweber, Wuppertal-Elberfeld; Edgar Enders, Cologne; Wilhelm Stendel, Wuppertal-Elberfeld, all of Germany

[73] Assignee: Bayer Aktiengesellschaft, Germany

[ * ] Notice: The portion of the term of this patent subsequent to Apr. 24, 1992, has been disclaimed.

[22] Filed: Dec. 28, 1973

[21] Appl. No.: 429,191

Related U.S. Application Data

[62] Division of Ser. No. 117,709, Feb. 22, 1971, Pat. No. 3,852,304.

[30] Foreign Application Priority Data

Feb. 26, 1970 Germany............................ 2009019

[52] U.S. Cl. ........................ 260/326.85; 260/239 B; 260/293.79
[51] Int. Cl.² ........................................ C07D 207/50
[58] Field of Search .................. 260/326.85, 293.79, 260/239 B

[56] References Cited

UNITED STATES PATENTS

| | | | |
|---|---|---|---|
| 3,729,485 | 4/1973 | Wollweber et al. | 260/326.85 |
| 3,803,134 | 4/1974 | Duerr et al. | 260/240 G |
| 3,821,204 | 6/1974 | Enders et al. | 260/240 F |

FOREIGN PATENTS OR APPLICATIONS

| | | | |
|---|---|---|---|
| 6,903,653 | 12/1969 | South Africa | 260/326.85 |
| 1,167,816 | 10/1969 | United Kingdom | 260/326.85 |

*Primary Examiner*—Raymond V. Rush

[57] ABSTRACT

Fluoroalkylphenylcycloamidines are useful for the control of ectoparasites in animals.

13 Claims, No Drawings

FLUOROALKYLPHENYLCYCLOAMIDINES AND THEIR PRODUCTION

This is a division of application Ser. No. 117,709 filed Feb. 22, 1971, now U.S. Pat. No. 3,852,304, dated Dec. 3, 1974.

The present invention is concerned with fluoroalkylphenylcycloamidines, processes for their production, veterinary compositions wherein one or more of said compounds is the active ingredient and the treatment of parasite infections in animals which comprises administering one or more of said compounds to the animal to be treated.

More particularly, the present invention is concerned with fluoroalkylphenylcycloamidines of the formula:

or a pharmaceutically acceptable non-toxic salt thereof, wherein
$n$ is 3, 4 or 5,
$m$ is 0, 1 or 2,
R is trifluoromethyl or difluoromethyl,
R' is halogen, such as fluorine, chlorine or bromine, alkyl of 1 to 4 carbon atoms or alkenyl of 2 to 4 carbon atoms, and
R'' is alkyl of 1 to 6 carbon atoms or alkenyl of 2 to 6 carbon atoms.

These compounds are useful for the control and treatment of animal ectoparasites particularly those of the class acarids.

Cyclic and acyclic phenylamidines are known. Up to now, only acyclic phenylamidines have been suggested as being effective against ticks. One of these compounds (I, South African Patent Specification No. 66/4135) was withdrawn because of its instability. Of the known amidines, compound II U.S. Pat. No. 3,189,648 is the closest compound to the chemical structure of the compounds of the present invention. However, said compound (II) is not known to exhibit activity.

It has now been discovered that by the introduction of a trifluoro- or difluoro-methyl group into the phenylcycloamidines strong activity against ticks results, particularly against tick strains which have become resistant to phosphoric acid. The compounds according to the invention are, moreover, stable when applied in cattle dip.

The haloalkenylphenylcycloamidines according to the invention are produced by reacting aniline derivatives of the formula:

wherein
R, R' and $m$ are as above defined, with lactams of the formula:

wherein
R'' and $n$ are as above defined, and
W is oxygen or sulphur
or their salts or reactive derivatives, optionally in the presence of condensation agents.

By reactive derivatives are meant, for example, compounds of the formula:

wherein
R'' and $n$ are as above defined, and
Z is a reactive ester or ether group.

These derivatives are obtained by the reaction of lactams or thiolactams of the formula:

wherein R'', W and n are as above defined, with inorganic acids (such as hydrogen chloride, boron trifluoride, sulphuric acid) or with inorganic or organic acid chlorides (such as phosphorus oxychloride, phosphorus pentachloride, phosgene, thionyl chloride, benzoyl bromide or a mixture of phosgene/aluminium chloride or phosgene/hydrogen chloride or phosgene/phosphorus oxychloride) or with trialkyl-oxoniumfluoroborates or with dialkylsulphates. The lactem esters are then usually present as complex salts of the formula:

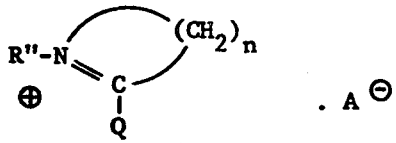

wherein
R'' and n are as above defined, and
Q and A are for example the following groups

| Q | A |
|---|---|
| O—POCl$_2$, POCl$_2$ | Cl |
| Cl | Cl, AlCl$_4$, HCl, POCl$_4$ |
| OSOCl | Cl |
| O—CO—C$_6$H$_5$, S—CO—C$_6$H$_5$ | Br, Cl |
| O—CO—Cl, S—CO—Cl | Cl |
| C$_6$H$_5$—SO$_2$—O—, Cl, Br | — |
| O-alkyl | BF$_4$ |
| S-alkyl | OSO$_2$—CH$_3$, Br, I, Cl |

These reactions can be carried out in such a manner that, from the lactams and the acid halide, there is first prepared the reactive lactim ester, optionally in the presence of solvents such as benzene, toluene or tetramethylenesulphone; the substituted aniline is then added dropwise and, optionally, the reaction mixture is afterwards heated for a time.

It is, however, also possible to proceed in such a manner that, to a mixture of lactam and substituted aniline, optionally in the presence of solvent, there is added dropwise the acid chloride, for example phosphorus oxychloride, and the reaction mixture is afterwards heated for a time.

It is also possible to react thiolactams of the formula:

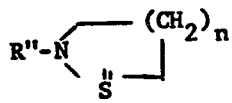

wherein R'' and n are as above defined, with substituted anilines in the presence of desulphurising agents, such as HgO, Ag$_2$O or Hg(CN)$_2$.

It is also possible to react acetals of the formula:

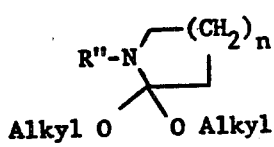

wherein R'' and n are as above defined, with substituted anilines.

Furthermore, it is possible to acylate anilines of the formula:

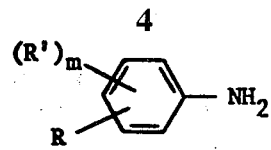

wherein R, R' and m are as above defined, with ω-haloalkane acid chlorides, convert these with phosphorus halides into the imide chlorides of the formula:

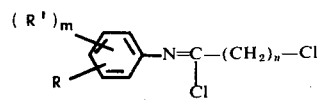

and react these with amines of the formula:

R'' — NH$_2$ wherein R'' is as above defined.

A further production route comprises heating arylisocyanates of the formula:

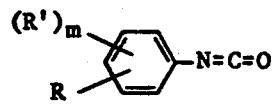

wherein R, R' and m are as above defined, with lactams of the formula:

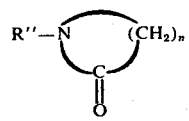

wherein R'' and n are as above defined.

The CO$_2$ evolution which occurs is a good indication of the reaction course.

Instead of isocyanates, carbamic acid chlorides of the formula:

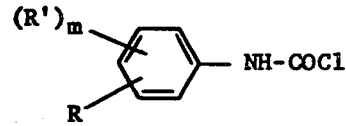

wherein R, R' and m are as above defined, can also be used.

Finally, cyclic amidines of the formula:

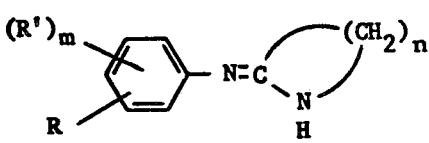

wherein

R, R', m and n are as above defined, can be reacted with alkylating agents of the formula:

B — R'' wherein
R'' is as above defined, and
B is a reactive ester group, such as halogen, arylsulphonyloxy, e.g. benzenesulphonyloxy, tosyloxy or alkylsulphonyloxy, e.g. methanesulphonyloxy.

Illustrative aniline derivatives which can be used as starting material include for example: 4-chloro-3-difluoromethylaniline, 4-bromo-3-difluoromethylaniline, 4-fluoro-3-difluoromethylaniline, 4-methyl-3-difluoromethylaniline, 5-methyl-3-difluoromethylaniline, 2-methyl-3-difluoro-methylaniline, 6-methyl-3-difluoromethylaniline, 6-chloro-3-difluoromethylaniline, 5-chloro-3-difluoromethylaniline, 2-chloro-3-difluoromethylaniline, 4-ethyl-3-difluoromethylaniline, 4-propyl-3-difluoromethylaniline, 4-butyl-3-difluoromethylaniline, 4-allyl-3-difluoromethylaniline, 3-difluoromethylaniline, 4-chloro-3-trifluoromethylaniline, 4-bromo-3-trifluoromethylaniline, 4-fluoro-3-trifluoromethylaniline, 4-methyl-3-trifluoromethylaniline, 5-methyl-3-trifluoromethylaniline, 2-methyl-3-trifluoromethylaniline, 6-methyl-3-trifluoromethylaniline, 6-chloro-3-trifluoromethylaniline, 5-chloro-3-trifluoromethylaniline, 2-chloro-3-trifluoromethylaniline, 4-ethyl-3-trifluoromethylaniline, 4-propyl-3-trifluoromethylaniline, 4-butyl-3-trifluoromethylaniline, 4-allyl-3-trifluoromethylaniline, 3-trifluoromethylaniline.

Illustrative alkylating agents which can be used include those of the formula:

B — R'' for example: butyl bromide, crotyl bromide, crotyl chloride, alkyl bromide, allyl chloride, dipropyl sulphate, tosyloxypropane, tosyloxypentane, tosyloxyhexane.

When the compounds of the invention are in the form of their salts, preferred salts include the hydrochlorides, sulphates, phosphates, nitrates, acetates and pahthalenedisulphonates.

The free bases and the salts exhibit strong acaricidal properties, particularly against acarids which as animal ectoparasites infest domesticated animals such as cattle and sheep. They are therefore well suited for the control of animal ectoparasites of the class acarids. As economically important ectoparasites of this nature which play a large part especially in tropical and sub-tropical countries, there are mentioned for example: the Australian and South American cattle tick Boophilus microplus, the South African cattle tick Boophilus decoloratus, both from the family of Ixodidae.

In the course of time, in various areas these ticks have become resistant to the phosphoric acid esters and carbamates used hitherto as control agents, so that the success of control there is rendered questionable. To safeguard an economic livestock husbandry in the infestation areas, there exists therefore a need for agents with which ticks, even of resistant strains, for example of the genus Boophilus, can be controlled with certainty. To a great extent resistant against the hitherto existing phosphoric acid ester agents and carbamates are, for example, in Australia the Ridgeland strain and the Biarra strain of Boophilus microplus. The active compounds according to the invention are equally well effective both against the normally sensitive and the resistant strains, for example of Boophilus. For example, on the adult forms they have a strong inhibitory effect on the depositing of eggs.

The compounds of the present invention may be used as such or in the form of veterinary compositions which comprise the compound in combination with a pharmaceutically acceptable (i.e. physiologically compatible with the animal to be treated) non-toxic inert diluent or carrier. Customary application methods include spraying, pouring, atomizing or application as a bath (dip). Any of the usual known additives such as disinfectants can also be included in the compositions of formulations. The techniques for producing such compositions and formulations are all per se well known.

EXAMPLE A

In-vitro test on ticks for inhibitory effect on egg depositing 3 parts of active compound are mixed with 7 parts of a mixture of equal parts by weight of ethyleneglycol monomethyl ether and nonylphenol polyglycol ether. The emulsion concentrate so obtained is diluted with water to the application concentration desired in each case.

Adult, gorged female ticks of the species Boophilus microplus (resistant) are immersed for one minute in this preparation of active compound. After immersion of, in each case, 10 female specimens of the various strains of ticks, the individual ticks are transferred into plastics dishes, the bottom of which is covered with a filter paper disc. After 35 days, the effectiveness of the preparation of active compound is determined by ascertaining the inhibition of the depositing of fertile eggs compared with the egg deposition of untreated control ticks. The effect is stated in %; 100% meaning that fertile eggs ceased to be deposited, and 0% meaning that the ticks have deposited eggs in normal manner like the untreated control ticks.

The active compounds investigated, the concentrations tried, the parasites tested and the findings obtained can be seen from the following Table:

Table 1

| | In-vitro test for ovicidal effect on ticks | |
|---|---|---|
| | Ovicidal effect against Boophilus microplus (Biarra strain) | |
| | 100% | >50% |
| Compounds | Inhibition with a concentration of | |
| Tests | active compound in % by weight of | |

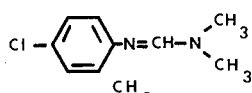

I (known)       0.5      0.08

Table 1-continued

| In-vitro test for ovicidal effect on ticks | | |
|---|---|---|
| | Ovicidal effect against Boophilus microplus (Biarra strain) | |
| | 100% | >50% |
| Compounds Tests | Inhibition with a concentration of active compound in % by weight of | |
| 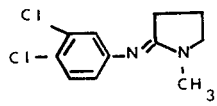<br>11 (known) | 0.2 | 0.08 |
| 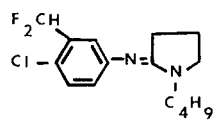 | 0.03 | 0.02 |
| 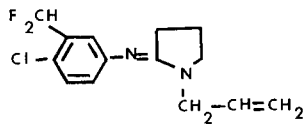 | 0.05 | 0.02 |

The following non-limitative examples more particularly illustrate the present invention:

EXAMPLE 1

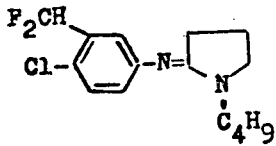

154 g (1.0 mole) phosphorus oxychloride are added dropwise at 20°C to a solution of 165 g (1.0 mole) 4-chloro-3-difluoromethylaniline and 155.3 g (1.0 mole) N-butylpyrrolidone in 1000 ml toluene, stirring is effected for 90 minutes at room temperature followed by heating under reflux for 4 hours until the splitting off of HCl has ended. After cooling, the toluene solution is decanted off, the residue is taken up in water, rendered alkaline with solution of sodium hydroxide, and the reaction product is extracted with a mixture of chloroform and ether. After evaporation of the solvent and distillation under reduced pressure, 166 g 1-butyl-2-(4-chloro-3-difluoromethylphenyl)-iminopyrrolidine of b.p. 154°–158°/0.2 mm Hg are obtained.

Compounds 2 through 32 set forth in Table 2 are produced in a manner analogous to the procedure described above.

Table 2

$$Ar-N=C\underset{\underset{R''}{N}}{\overset{(CH_2)_n}{\diagup}}$$

| | Ar | n | R'' | b.p. (°C)/mm Hg |
|---|---|---|---|---|
| 2. | F₂HC–⟨Cl⟩– | 3 | —CH₂—CH=CH₂ | 148°/0.2 |
| 3. | F₂HC–⟨Cl⟩– | 3 | C₃H₇ | 148–150°/0.2 |

Table 2-continued

| | Ar | n | R'' | b.p. (°C)/mm Hg |
|---|---|---|---|---|
| 4. | F₂HC–C₆H₃(Cl)– | 3 | C₄H₉ | 146–148°/0.9 |
| 5. | F₂CH,Cl–C₆H₃– | 3 | CH₂—CH=CH—CH₃ | 158°/0.3 |
| 6. | F₂CH,Cl–C₆H₃– | 3 | CH₂—C(CH₃)=CH₂ | 149–153°/0.2 |
| 7. | F₂HC,Cl–C₆H₃– | 3 | C₆H₁₃ | 172–174°/0.2 |
| 8. | F₃C,Cl–C₆H₃– | 3 | C₄H₉ | 150–155°/0.05 |
| 9. | F₃C,Cl–C₆H₃– | 3 | CH₂—CH=CH₂ | 138–140°/0.1 |
| 10. | F₃C,Cl–C₆H₃– | 3 | C₃H₇ | 144–148°/0.1 |
| 11. | F₃C,Cl–C₆H₃– | 3 | CH₂—CH=CH—CH₃ | 156–158°/0.2 |
| 12. | F₃C,Cl–C₆H₃– | 3 | CH₂—C(CH₃)=CH₂ | 152–154°/0.2 |
| 13. | F₃C,Cl–C₆H₃– | 3 | C₅H₁₁ | 162–164°/0.2 |
| 14. | F₃C–C₆H₄– | 3 | C₄H₉ | 130–132°/0.2 |
| 15. | CF₃–C₆H₄– | 3 | C₄H₉ | 125–126°/0.2 |

Table 2-continued
$$Ar-N=C\underset{\underset{R''}{N}}{\overset{(CH_2)_n}{\diagup}}$$
| | Ar | n | R'' | b.p. (°C)/mm Hg |
|---|---|---|---|---|
| 16. | 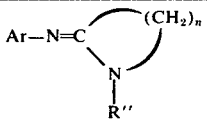 | 3 | C₄H₉ | 160–164°/0.2 |
| 17. | 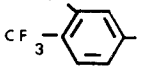 | 3 | C₃H₇ | 150–152°/0.2 |
| 18. | 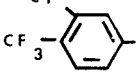 | 3 | CH₂—CH=CH₂ | 147–153°/0.03 |
| 19. | 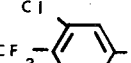 | 4 | C₄H₉ | 162–164°/0.2 |
| 20. | 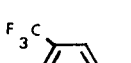 | 5 | C₄H₉ | 172–176°/0.2 |
| 21. | 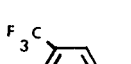 | 4 | C₄H₉ | 158–160°/0.2 |
| 22. | 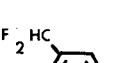 | 5 | C₄H₉ | 170–175°/0.2 |
| 23. | 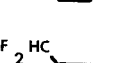 | 3 | CH₃ | 117–121°/0.5 |
| 24. | 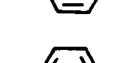 | 3 | CH₃ | 127–130°/1.0 |
| 25. | 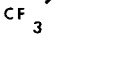 | 3 | CH₃ | 110–118°/0.02 |
| 26. |  | 3 | C₂H₅ | 126–130°/0.5 |
| 27. |  | 3 | C₃H₇ | 132–136°/0.03 |

Table 2-continued $$Ar-N=C\underset{\underset{R''}{N}}{\overset{(CH_2)_n}{\diagup}}$$

| | Ar | n | R'' | b.p. (°C)/mm Hg |
|---|---|---|---|---|
| 28. | 4-Cl, 3-CF$_3$-phenyl | 3 | CH$_2$—CH=CH$_2$ | 123–132°/0.03 |
| 29. | 4-Cl, 3-CF$_3$-phenyl | 3 | (CH$_3$)$_2$CH | 115–123°/0.02 |
| 30. | 4-Cl, 3-CF$_3$-phenyl | 3 | C$_4$H$_9$ | 133–139°/0.03 |
| 31. | 3-CF$_3$, 4-Cl-phenyl | 3 | CH$_3$ | 143–147°/1.0 |
| 32. | 3,5-bis(CF$_3$)-phenyl | 3 | CH$_2$—CH=CH$_2$ | 104–112°/0.03 |

EXAMPLE 33

A solution of 9.9 g phosgene in 75 ml toluene is added dropwise to a solution of 16.5 g 4-chloro-3-difluoromethylaniline and 15.5 g N-butylpyrrolidone in 25 ml toluene, stirring is effected at 20° for 90 minutes followed by heating under reflux for 4 hours. After the working up described in Example 1, 13.2 g 1-butyl-2-(4-chloro-3-difluoromethylphenyl)-iminopyrrolidine of b.p. 154°–158°/0.2 mm Hg are obtained.

EXAMPLE 34

A solution of 31.4 g N-butylthiopyrrolidone and 40 g 4-chloro-3-difluoromethylaniline in 40 ml ethanol is, with addition of 75 g mercury oxide, stirred vigorously for 8 hours at 0° and then for 15 hours at 80°. Suction filtration from the precipitate is effected, the residue is distilled in a vacuum, and 12.4 g 1-butyl-2-(4-chloro-3-difluoromethylphenyl)-iminopyrrolidine of b.p. 154°–158°/0.2 mm Hg are obtained.

EXAMPLE 35

8.5 g (0.11 mole) allyl chloride are added dropwise at 20° to 24.5 g (0.1 mole) 4-chloro-3-difluoromethyliminopyrrolidine dissolved in 100 ml tetrahydrofuran and heating under reflux is subsequently carried out overnight. Suction filtration from the precipitate is effected. The filtrate is washed several times with water. After separation of the organic phase, evaporation is effected and, after distillation at b.p. 130°–160°/0.2 mm Hg, a mixture of the formulae

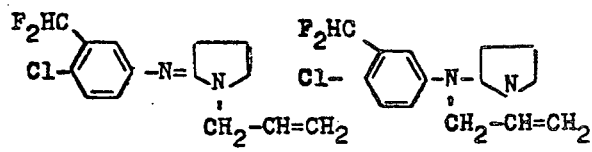

from which, after column distillation,1-butyl-2-(4-chloro-3-difluoromethylphenyl)-iminopyrrolidine, b.p. 146°–147°/0.05 mm Hg, was able to be obtained pure. yield 6.8 g.

EXAMPLE 36

18.5 g 4-chloro-3-trifluoromethylaniline and 21.5 g N-butylpyrrolidonediethylacetal (prepared from triethyloxoniumfluoroborate and butylpyrrolidone) are heated to 110°–140°, the alcohol liberated in the reaction distilling off in 30 minutes. The residue gives, after distillation in a vacuum, 21.3 g 1-butyl-2-(4-chloro-3-trifluoromethylphenyl)-iminopyrrolidine, b.p. 150°–155°/0.05 mm Hg.

EXAMPLE 37

50 ml butylcaprolactam and 25 ml 4-chloro-3-trifluoromethylisocyanate are heated under reflux until the $CO_2$ evolution has ceased. The reaction product is distilled in a vacuum and 12.5 g 1-butyl-2-(4-chloro-3-trifluoromethylphenyl)-iminoazacycloheptane, b.p. 172°–176°/0.2 mm Hg, are obtained.

EXAMPLE 38

31.4 g (0.2 mole) γ-chlorobutyric acid chloride are added to a solution of 37 g (0.2 mole) 4-chloro-3-trifluoroaniline in 350 ml benzene, heating under reflux is effected for 2 hours, followed by cooling, addition of 48.7 g phosphorus pentachloride, and gradual heating to reflux. After cessation of hydrogen chloride evolution, the phosphorus oxychloride formed is distilled off in a vacuum and 1,4-dichloro-1-(4-chloro-3-trifluorophenylimino)-butane is obtained as hardly volatile oil. This is taken up in 100 ml benzene, added dropwise at 20° to 33g (0.45 mole) butylamine in 200 ml benzene, and heated under reflux for 2 hours. Pouring into ice water is effected, followed by rendering alkaline with solution of sodium hydroxide and working up analogously with Example 1. 43 g 1-butyl-2-(4-chloro-3-trifluoromethylphenyl)-iminopyrrolidine, b.p. 150°–155°/0.05 mm Hg, are obtained.

What is claimed is:

1. A compound of the formula:

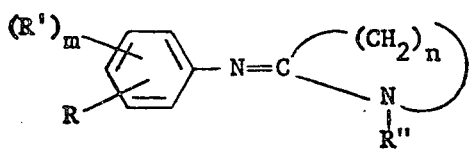

or a pharmaceutically acceptable non-toxic salt thereof, wherein
   $n$ is 3, 4 or 5,
   $m$ is 1,
   R is trifluoromethyl or difluoromethyl
   R' is fluorine, chlorine or bromine, alkyl of 1 to 4 carbon atoms or alkenyl of 2 to 4 carbon atoms and
   R'' is —$CH_2$—CH=$CH_2$; —$CH_2$—CH=CH—$CH_3$; or

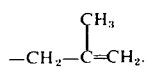

2. A compound according to claim 1 wherein R' is fluorine, chlorine or bromine.
3. A compound according to claim 2 wherein R' is chlorine.
4. The compound according to claim 1 wherein $n$ is 3, $m$ is 1, R is difluoromethyl, R' is chlorine, and R'' is —$CH_2$—CH=$CH_2$.
5. The compound according to claim 1 of the formula:

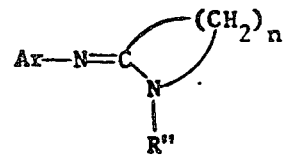

wherein

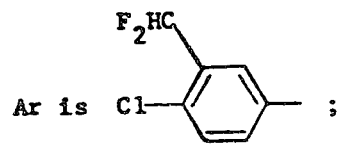

R'' is —$CH_2$—CH=$CH_2$; and $n$ is 3.

6. The compound according to claim 1 of the formula:

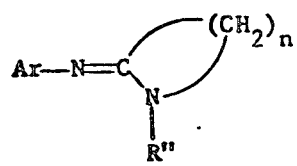

wherein Ar is

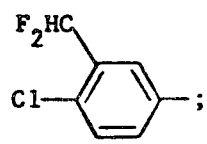

R'' is —$CH_2$—CH=CH—$CH_3$; and $n$ is 3.

7. The compound according to claim 1 of the formula:

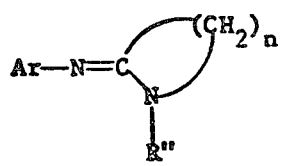

wherein Ar is

Ar is 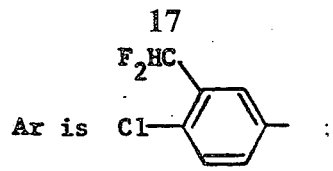

R'' is —CH₂—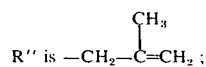—CH₂ ;

and $n$ is 3.

8. The compound according to claim 1 of the formula:

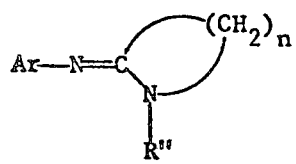

wherein Ar is

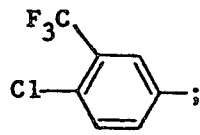

R'' is —CH₂—CH=CH₂; and $n$ is 3.

9. The compound according to claim 1 of the formula:

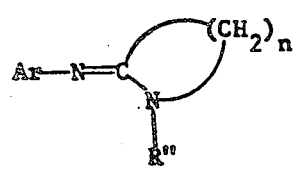

wherein Ar is

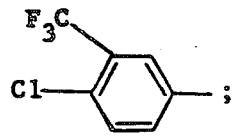

R'' is —CH₂—CH=CH₃; and $n$ is 3.

10. The compound according to claim 1 of the formula:

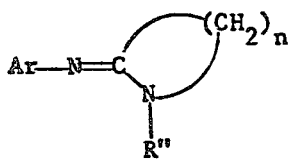

wherein Ar is

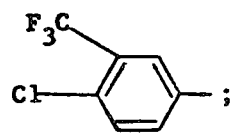

R'' is —CH₂—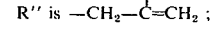—CH₂ ;

and $n$ is 3.

11. The compound according to claim 1 of the formula:

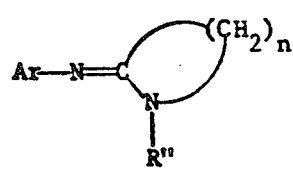

wherein Ar is

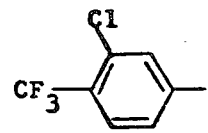

R'' is —CH₂—CH=CH₂; and $n$ is 3.

12. The compound according to claim 1 of the formula:

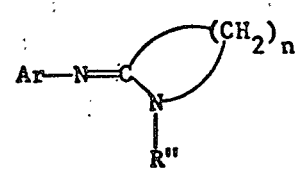

wherein Ar is

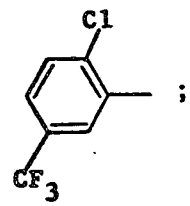

R'' is—CH₂—CH=CH₂; and $n$ is 3.

13. The compound of the formula:
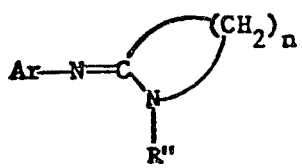
wherein Ar is
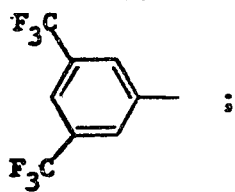
R'' is —CH$_2$—CH=CH$_2$; and $n$ is 3.